US012390439B2

(12) United States Patent
Bhadgale

(10) Patent No.: US 12,390,439 B2
(45) Date of Patent: Aug. 19, 2025

(54) ORAL LIQUID FORMULATION OF METHOCARBAMOL

(71) Applicant: Liqmeds Worldwide Limited, Weedon (GB)

(72) Inventor: Mahesh Bhadgale, Pune (IN)

(73) Assignee: Liqmeds Worldwide Limited, Weedon (GB)

( * ) Notice: Subject to any disclaimer, the term of this patent is extended or adjusted under 35 U.S.C. 154(b) by 0 days.

(21) Appl. No.: 19/012,616

(22) Filed: Jan. 7, 2025

(65) Prior Publication Data

US 2025/0134846 A1    May 1, 2025

Related U.S. Application Data

(63) Continuation-in-part of application No. PCT/IB2024/059865, filed on Oct. 9, 2024.

(30) Foreign Application Priority Data

Oct. 10, 2023  (IN) .............................. 202321067771
Apr. 30, 2024  (IN) .............................. 202421034276

(51) Int. Cl.
| | |
|---|---|
| *A61K 31/27* | (2006.01) |
| *A61K 9/00* | (2006.01) |
| *A61K 9/10* | (2006.01) |
| *A61K 47/02* | (2006.01) |
| *A61K 47/10* | (2017.01) |
| *A61K 47/12* | (2006.01) |
| *A61K 47/26* | (2006.01) |
| *A61K 47/36* | (2006.01) |

(52) U.S. Cl.
CPC ............ *A61K 31/27* (2013.01); *A61K 9/0095* (2013.01); *A61K 9/10* (2013.01); *A61K 47/02* (2013.01); *A61K 47/10* (2013.01); *A61K 47/12* (2013.01); *A61K 47/26* (2013.01); *A61K 47/36* (2013.01)

(58) Field of Classification Search
CPC .......... A61K 31/27; A61K 9/10; A61K 47/02; A61K 47/10; A61K 47/12; A61K 47/26
See application file for complete search history.

(56) References Cited

U.S. PATENT DOCUMENTS 3,699,230 A * 10/1972 Beauchamp, Jr. ..... A61K 47/26
                                                            514/479

FOREIGN PATENT DOCUMENTS

| CN | 100339072 C | 9/2007 | |
|---|---|---|---|
| EP | 1930003 A1 * | 6/2008 | ............. A61K 31/27 |

OTHER PUBLICATIONS

Wikilecture (phosphate buffer, 2022. (Year: 2022).*
The Handbook of Pharmaceutical Excipients, 5th edition 2006 (http://www.gmpua.com/RD/RD/HandbookPharmaceutical%20Excipients.pdf). (Year: 2006).*
World Health Organization, 2022, Musculoskeletal conditions. (Year: 2022).*
Zhou Yan-bin et al. "HPLC determination of methocarbamol in human plasma and its relative bioavailability", Chinese Journal of Pharmaceutical Analysis, vol. 0(5), 702-705 (2008).
Shivani Kalokhe et al., "Development and Validation of a Stability-Indicating High-Performance Liquid Chromatographic Method for the Quantification of Methocarbamol and Its Impurities in Pharmaceutical Dosage Forms", Journal of Chromatographic Science, vol. 59, issue 6: 555-565 (2021).
Bobby N. Pruitt, "Methocarbamol Suspension for the Treatment of Rhabdomyolysis in Equines", International Journal of Pharmaceutical Compounding, vol. 17(5): 384-387 (2013), Abstract.
Robaxin® and Robaxin®-750 (Methocarbamol) Tablets, Prescribing Information, Schwarz Pharma, Inc. (2003), 6 pages.
Bobby N. Pruitt, "Methocarbamol Suspension for the Treatment of Rhabdomyolysis in Equines", International Journal of Pharmaceutical Compounding, vol. 17(5): 384-387 (2013).

\* cited by examiner

*Primary Examiner* — James H Alstrum-Acevedo
*Assistant Examiner* — Manahil Mirghani Ali Abdalhameed
(74) *Attorney, Agent, or Firm* — Merchant & Gould P.C.; Daniel R. Evans; Jenna L. Logsdon

(57) ABSTRACT

Disclosed herein is an oral liquid formulation of methocarbamol, which may be in the form of suspension. Also disclosed herein is a process for the preparing the oral liquid formulation of methocarbamol, and the use of the oral liquid formulation for the treatment of acute musculoskeletal pain.

20 Claims, No Drawings

ORAL LIQUID FORMULATION OF METHOCARBAMOL

RELATED APPLICATION

This application is a continuation-in-part of International Application No. PCT/IB2024/059865, filed on Oct. 9, 2024, which claims priority to Indian Patent Application Nos. 202321067771 filed on Oct. 10, 2023, and 202421034276 filed on Apr. 30, 2024.

FIELD

The disclosed subject matter relates to an oral liquid formulation of methocarbamol. More particularly, the disclosed subject matter relates to an oral liquid formulation of methocarbamol in the form of suspension. Disclosed herein is a process for the preparation of said oral liquid formulation of methocarbamol, and use of said oral liquid formulation of methocarbamol for the treatment of acute musculoskeletal pain.

BACKGROUND

A muscle spasm also known as a charley horse, muscle cramp or twitch is a sudden, involuntary movement in one or more muscles. Most commonly it occurs in the thighs, calves, feet, hands, and arms. They can also occur in the abdomen or along the rib cage. Muscle spasms are typically harmless, but they may result in an inability to use the affected muscle for a short period of time. Muscle spasms can occur due to several causes, including a lack of nutrients, muscular tension or stress, dehydration, overuse of the muscle, increased demand of blood flow, or various underlying medical conditions.

Skeletal muscle relaxants are class of drugs that are used to relax and reduce tension in the muscles. They are more simply referred to as muscle relaxants. Skeletal muscle relaxants are used for a variety of conditions, including musculoskeletal conditions such as low back pain, and spastic conditions such as multiple sclerosis, spinal cord injuries, and cerebral palsy. Some muscle relaxants work in brain or spinal cord to block or dampen down excessively stimulated nerve pathway. The skeletal muscle relaxants are generally classified into two categories: centrally acting skeletal muscle relaxants, which work by depressing neuron activity in the CNS, and direct acting skeletal muscle relaxants, which prevent the release of calcium ions from muscle cells. Centrally acting muscle relaxants include cyclobenzaprine, methocarbamol, metaxalone, and chlorzoxazone, whereas among direct acting skeletal muscle relaxants, dantrolene.

Methocarbamol is a centrally acting skeletal muscle relaxant approved for the treatment of acute musculoskeletal pain. Methocarbamol is used with rest, physical therapy, and other measures to relax muscles, and relieve pain and discomfort caused by strains, sprains, and other muscle injuries. Methocarbamol treats muscle pain, and stiffness. It works by calming overactive nerves in your body, which helps your muscles relax. Methocarbamol is commercially available, in particular as an oral tablet, and parenteral, under the trade names ROBAXIN, and ROBAXIN-750.

The most common way people take medications is orally. Oral medications come in the form of solid tablets, capsules, chewable tablets or lozenges to be swallowed whole or sucked on, or as drinkable liquids such as drops, syrups, suspensions or solutions. The oral medications can be swallowed, chewed, or placed under the tongue to dissolve. Various oral formulations are available in the market. Oral medication is the common form of drug administration because of its advantages such as convenience of drug administration via the oral route, patient preference, cost-effectiveness, and ease of large-scale manufacturing of oral dosage forms. However, an oral liquid dosage formulation providing many advantages over solid dosage form like better patient compliance especially to pediatric, geriatric, or to patients having difficulty in swallowing, they are available in different flavors which masks the taste of drug, they are more quickly absorbed on administration and hence give quicker onset of action.

Bioavailability refers to the extent a substance or drug becomes completely available to its intended biological destinations. More accurately, bioavailability is a measure of the rate and fraction of the initial dose of a drug that successfully reaches either, the site of action or the bodily fluid domain from which the drug's intended targets have unimpeded access. There are the various factors which affects bioavailability. For any oral dosage form, the ultimate goal is the release of the drug into the GI tract for absorption and subsequent delivery to the target organ via the bloodstream. The oral tablet formulation involves disintegration followed by dissolution then absorption of drug in the solution form. However, in liquid dosage forms faster absorption as there is no need of disintegration step and hence quicker onset of action. Hence, liquid formulations have a higher bioavailability than solid oral dosage forms. Moreover, the liquid dosage forms are useful for the people who find it difficult to swallow the solid forms of medication.

Currently, there is no oral liquid formulation of methocarbamol in the market. Hence, there is need to develop an oral liquid formulation of methocarbamol which will overcome the above stated disadvantages of solid dosage form.

Thus, the inventor has obtained an oral liquid formulation of methocarbamol that aims to overcome problems cited above by preparing an oral liquid formulation of methocarbamol as described herein.

Objectives

An objective disclosed herein relates to the development of an oral liquid formulation of methocarbamol.

Another objective disclosed herein is an oral liquid formulation of methocarbamol for treatment of acute musculoskeletal pain.

Yet another objective disclosed herein is to provide an oral liquid formulation of methocarbamol which is having dose accuracy, flexibility, and uniformity of dosage.

Yet another objective disclosed herein is to provide an oral liquid formulation of methocarbamol which is stable, and provides better patient compliance.

Yet another objective disclosed herein is to provide an oral liquid formulation of methocarbamol which gives faster absorption, and quicker onset of action.

SUMMARY

Disclosed herein is an oral liquid formulation of methocarbamol.

A main aspect disclosed herein relates to an oral liquid formulation of methocarbamol, comprising: methocarbamol in an amount of from about 25 mg/mL to about 400 mg/mL; a suspending agent; one or more pH modifying agent; one or more pharmaceutically acceptable excipients; and at least one vehicle; wherein the oral liquid formulation has a pH of from about 2 to about 7.

Another aspect disclosed herein relates to a process for preparing an oral liquid formulation of methocarbamol.

One more aspect disclosed herein relates a method for the treatment of acute musculoskeletal disorders associated with painful muscle spasms by administering the oral liquid formulation of methocarbamol disclosed herein.

DETAILED DESCRIPTION

Disclosed herein is an oral liquid formulation of methocarbamol.

Before elaborating on the disclosed formulation, it is to be understood that the disclosed formulation is not limited to particularly exemplified examples or process parameters that may, of course, vary. It is also to be understood that the terminology used herein is to describe particular embodiments of the disclosed formulation, and is not intended to limit the scope of the claimed formulation in any manner.

The detailed description set forth below is intended as a description of exemplary embodiments and is not intended to represent the only forms in which the exemplary embodiments may be constructed and/or utilized. The description sets forth the functions and the sequence of steps for constructing and/or operating the exemplary embodiments. However, it is to be understood that the same or equivalent functions and sequences which may be accomplished by different exemplary methods are also intended to be encompassed within the spirit and scope of the subject matter claimed herein.

As defined herein, all scientific and technical terms used herein have the same meaning as understood by one of ordinary skill in the art of pharmaceutical sciences.

Although any process and materials similar or equivalent to those described herein can be used in the practice or testing of the disclosed formulation, the preferred methods and materials are now described.

As used herein, the singular forms "a," "an" and "the" specifically also encompass the plural forms of the terms to which they refer, unless the content clearly dictates otherwise. The term "about" is used herein to means approximately, in the region of, roughly, or around.

As stated herein, the expressions "comprise(s)" and "comprising" have their customary meaning. When used in the context of a process/method, the term "comprising" means that the process/method includes at least the recited step, but may include additional steps. When used in the context of a formulation, the term "comprising" means that the formulation includes at least the recited features or components, but may also include additional features or components.

One will understand that the expression "consisting of" may replace the expression "comprising" for a claimed formulation, process, or method.

One will further understand that the expression "consisting essentially of" may replace the expression "comprising" for a claimed formulation, process, or method.

As used herein, the term "active agent" can be understood to include any substance or formulation or combination of substances or composition of matter when administered to a human or animal subject, induces a desired pharmacologic and/or physiologic effect by local and/or systemic action. The terms are used interchangeably herein: "active", "drug", "therapeutic agent", "active pharmaceutical agent", and "active ingredient".

A "therapeutically effective amount" or "effective amount" is that amount of a pharmaceutical agent to achieve a pharmacological effect. The term "therapeutically effective amount" includes, for example, a prophylactically effective amount.

As used herein, the term "therapeutically effective amount" can be understood to include an amount of methocarbamol that is effective in preventing or ameliorating a condition requiring an adjunct to rest, physical therapy, and other measures for the relief of discomfort associated with acute, painful musculoskeletal conditions.

As used herein the word "liquid formulation" refers to liquid oral formulation like solution, suspension or emulsion, more preferably in the form of suspension.

As used herein, the terms "dose" and "dosage" can be understood to mean a specific amount of active or therapeutic agents for administration.

The term "about" is used synonymously with the term "approximately." As one of ordinary skill in the art would understand, the exact boundary of "about" will depend on the component of the formulation. Illustratively, the use of the term "about" indicates that values slightly outside the cited values, i.e., plus or minus 0.1% to 10%, which are also effective and safe. Thus, formulations slightly outside the cited ranges are also encompassed by the scope of the present claims. However, when the term "about" is used in connection with pH, it should be considered as plus or minus 2 unit of the pH value, or alternatively as plus or minus 0.1% to 10% of the stated pH value.

By the term "pH", as used herein, is meant "apparent pH" wherein the pH measurement is carried out on the methocarbamol containing formulation in final form, for example, by measuring the pH of the formulation.

The term "pH modifying agent" used herein refers to agents which provide stability and pH control to the pharmaceutical formulations. Herein the words "pH modifying agent" and "buffering agent" are used interchangeably.

The term "antimicrobial agent" used herein refers to a chemical substance that is used to preserve pharmaceuticals from decomposition or fermentation by preventing the growth of microorganisms. Herein the words "antimicrobial agent" and "preservatives" are used interchangeably.

As used herein, the term "viscosifying agent" can be interchangeably used with the term "viscosity modifying agent" and "thickening agent" as all are the same.

As per one preferred embodiment, the term "ready-to-use" used herein is defined as the suspension that can administered directly to a patient for a treatment without the steps such as reconstitution or dilution.

As stated herein the term "RTU" refers to ready-to-use and can interchangeably use for the "ready-to-use" phrase.

An embodiment disclosed herein relates to an oral liquid formulation of methocarbamol, comprising: methocarbamol in an amount of from about 25 mg/mL to about 400 mg/mL; a suspending agent; one or more pH modifying agent; one or more pharmaceutically acceptable excipients; and at least one vehicle; wherein the oral liquid formulation has a pH of from about 2 to about 7.

As per one embodiment of the oral liquid formulation, an oral liquid formulation of methocarbamol has a particle size distribution of: D(0.10) not more than 25 μm, not more than 20 μm, or not more than 10 μm, D(0.50) not more than 50 μm, not more than 40 μm, or not more than 25 μm, and D(0.90) not more than 150 μm, not more than 100 μm, or not more than 70 μm, wherein the particle size determinations performed using suitable instrumentation, e.g., by Malvern method.

As per preferred embodiment of the oral liquid formulation of methocarbamol has a particle size distribution of: D(0.10)-6.166 μm, D(0.50)-17.985 μm, and D(0.90)-47.679 μm.

As per one embodiment of the oral liquid formulation, methocarbamol can be present in the formulation in an amount of from about 1 mg/mL to about 500 mg/mL, and all values in between, such as from about 1 mg/mL to about 400 mg/mL, from about 1 mg/mL to about 300 mg/mL, from about 1 mg/mL to about 200 mg/mL, from about 10 mg/mL to about 500 mg/mL, from about 10 mg/mL to about 400 mg/mL, from about 10 mg/mL to about 300 mg/mL, from about 10 mg/mL to about 200 mg/mL, from about 25 mg/mL to about 500 mg/mL, from about 25 mg/mL to about 400 mg/mL, from about 25 mg/mL to about 300 mg/mL, or from about 25 mg/mL to 200 mg/mL.

As per one embodiment of the oral liquid formulation, an antimicrobial agent can be selected from but not limited to benzoic acid, potassium sorbate, sodium benzoate, chlorobutanol, ethanol, butyl paraben, propyl paraben, methyl paraben, ethyl paraben, benzalkonium chloride, benzethonium chloride, benzyl alcohol, chlorobutanol, m-cresol, myristyl gamma picolinium chloride, phenol, 2-phenoxyethanol, phenyl mercuric nitrate, phenyl ethyl alcohol, and ethylenediaminetetraacetic acid (EDTA) or EDTA salts thereof, or any combination thereof.

As per preferred embodiment of the oral liquid formulation, an antimicrobial agent is sodium benzoate.

As per one embodiment of the oral liquid formulation, an antimicrobial agent (e.g., sodium benzoate) can be used in the range from about 0.01 mg/mL to about 20 mg/mL, and all values in between, such as from about 0.01 mg/mL to about 15 mg/mL, from about 0.05 mg/mL to about 15 mg/mL, and from about 0.05 mg/mL to about 10 mg/mL.

As per one embodiment of the oral liquid formulation, the suspending agent can be selected from but not limited to xanthan gum, guar gum, locust bean gum, gum tragacanth, a combination of microcrystalline cellulose, and sodium carboxymethylcellulose, microcrystalline cellulose, sodium carboxymethylcellulose, polyvinylpyrrolidone, hydroxypropyl cellulose, and magnesium aluminum silicate, or any combination thereof.

As per preferred embodiment of the oral liquid formulation, the suspending agent is magnesium aluminum silicate.

As per one embodiment of the oral liquid formulation, the suspending agent (e.g., magnesium aluminum silicate) can be used in the range from about 1 mg/mL to about 25 mg/mL, and all values in between, such as from about 1 mg/mL to about 20 mg/mL, from about 1 mg/mL to about 15 mg/mL, and from about 1 mg/mL to about 10 mg/mL.

As per one embodiment of the oral liquid formulation, the viscosity modifying agent can be selected from methyl cellulose, hydroxyethyl cellulose, bentonite, hectorite, magnesium aluminum silicate, microcrystalline cellulose, sodium carboxymethyl cellulose, hydroxy propyl methyl cellulose (HPMC), xanthan gum, acacia, tragacanth, alginates, guar gum, and colloidal silicon dioxide, or any combination thereof.

As per preferred embodiment of the oral liquid formulation, the viscosity modifying agent is sodium carboxymethylcellulose.

As per one embodiment of the oral liquid formulation, the viscosity modifying agent (e.g., sodium carboxymethylcellulose) can be used in the range from about 1 mg/mL to about 25 mg/mL, and all values in between, such as from about 1 mg/mL to about 20 mg/mL, from about 1 mg/mL to about 15 mg/mL, and from about 1 mg/mL to about 10 mg/mL.

As per one embodiment of the oral liquid formulation, one or more pH modifying agent can be selected from sodium citrate, sodium acetate trihydrate, phosphate, citric acid, citric acid monohydrate, tromethamine (tris), succinic acid, succinate, histidine, glycine, arginine, malic, malate, tartaric acid, tartrate, acetic acid, acetate, benzoic acid, benzoate, gluconic acid, gluconate, glyceric acid, glycerate, lactic acid, lactate, adipic, ascorbic, ascorbate, carbonic acid, bicarbonate, carbonate, glutamic, ammonium chloride, trisodium citrate dihydrate, triethanolamine, and salts or acids thereof, or any combination thereof.

As per one embodiment of the oral liquid formulation, one or more pH modifying agent can be preferably combination of two pH modifying agents. As per preferred embodiment of the oral liquid formulation, a combination of trisodium citrate dihydrate, and citric acid monohydrate is used as pH modifying agent.

As per one embodiment of the oral liquid formulation, trisodium citrate dihydrate or one or more pH modifying agent can be used in the range from about 0.5 mg/mL to about 30 mg/mL, and all values in between, such as from about 0.5 mg/mL to about 20 mg/mL, from about 1 mg/mL to about 20 mg/mL, and from about 1 mg/mL to about 15 mg/mL.

As per one embodiment of the oral liquid formulation, citric acid monohydrate or one or more pH modifying agent can be used in the range from about 0.5 mg/mL to about 30 mg/mL, and all values in between, such as from about 1 mg/mL to about 30 mg/mL, from about 1 mg/mL to about 25 mg/mL, and from about 1 mg/mL to about 20 mg/mL.

As per one embodiment of the oral liquid formulation, one or more pH modifying agent present in the suspension are citric acid monohydrate and trisodium citrate dihydrate, where the ratio of citric acid monohydrate:trisodium citrate dihydrate is between about 4:3 to 4:2, 4:3 to 1:1, 3:1.5 to 2.5:1, 2:2 (e.g., 1) to 6:2 (e.g., 3), 2:1 (e.g., 2) to 6:2 (e.g., 3). Alternatively, the ratio of citric acid monohydrate:trisodium citrate dihydrate ranges from about 2 to about 4, from about 2 to about 3, or the ratio is about 2.8.

As per another embodiment of the oral liquid formulation, one or more pharmaceutically acceptable excipients can be selected from an antimicrobial agent, a viscosity modifying agent, a humectant, a sweetening agent, a flavouring agent, or any combination thereof.

As per another embodiment of the oral liquid formulation, one or more pharmaceutically acceptable excipients can be used in the range from about 0.01 mg/mL to about 500 mg/mL, and all values in between, such as from about 0.1 mg/mL to about 400 mg/mL, and from about 0.5 mg/mL to about 400 mg/mL.

As per one embodiment of the oral liquid formulation, the humectant can be selected from glycerol, hyaluronic acid, salicylic acid, alpha hydroxy acids (AHAs), such as glycolic acid, and lactic acid, propylene glycol, honey, and sorbitol, or any combination thereof.

In one aspect of the oral liquid formulation, the humectant is glycerol.

As per one embodiment of the oral liquid formulation, the humectant (e.g., glycerol) can be used in the range from about 1 mg/mL to about 700 mg/mL, and all values in between, such as from about 1 mg/mL to about 500 mg/mL, from about 100 mg/mL to about 500 mg/mL, and from about 100 mg/mL to about 400 mg/mL.

As per one embodiment of the oral liquid formulation, the sweetening agent can be selected from but not limited to glucose, sucralose, trehalose, fructose, xylose, dextrose, galactose, tagatose, maltose, sucrose, glycerol, dulcitol, mannitol, lactitol, sorbitol, xylitol, saccharine or the corresponding sodium, potassium or calcium salt, cyclamate or the corresponding sodium or calcium salt, aspartame, or acesulfame or the potassium salt thereof, ammonium glycyrrhizinate, alitame, inulin, isomalt, neohesperidin dihydrochalcone, neotame, thaumatin, and the like, or any combination thereof.

In one aspect of the oral liquid formulation, the sweetening agent is sucralose.

As per one embodiment of the oral liquid formulation, the sweetening agent (e.g., sucralose) can be used in the range from about 1 mg/mL to about 50 mg/mL, and all values in between, such as from about 1 mg/mL to about 30 mg/mL, from about 1 mg/mL to about 25 mg/mL, and from about 10 mg/mL to about 25 mg/mL.

As per one embodiment of the oral liquid formulation, the flavoring agent can be selected from but not limited to vanilla, citrus oil, including lemon, orange, grape, lime, and grapefruit, and fruit essences, including apple, banana, pear, peach, strawberry, raspberry, cherry, plums pineapple, apricot, peppermint, tutti frutti flavor, and so forth, and the like, or any combination thereof.

In one aspect of the oral liquid formulation, the flavoring agent is tutti frutti flavor.

As per one embodiment of the oral liquid formulation, the flavoring agent (e.g., tutti frutti flavor) can be used in the range from about 0.01 mg/mL to about 5 mg/mL, and all values in between, such as from about 0.05 mg/mL to about 5 mg/mL, from about 0.5 mg/mL to about 5 mg/mL, and from about 0.5 mg/mL to about 3 mg/mL.

Vehicle can be considered as any inert substance, or mixture of substances, added to increase the volume of the liquid formulation to make the oral liquid formulation disclosed herein in a suitable form.

As per one embodiment of the oral liquid formulation, at least one vehicle can be selected from purified water, glycerol, phosphate buffer, propylene glycol, glycerin containing buffers, or any combination thereof.

In one aspect of the oral liquid formulation, the vehicle is purified water.

As per one embodiment of the oral liquid formulation, the vehicle (e.g., purified water) can be used to adjust the final volume of the formulation.

As per one embodiment of the oral liquid formulation, the pH is in the range from about 2 to about 7, more preferably in the range from about 3 to about 6, and most preferably in the range from about 3 to about 5.

An embodiment disclosed herein relates to an oral liquid formulation comprising about 25 mg/mL to about 200 mg/mL methocarbamol; an antimicrobial agent; a suspending agent; a viscosity modifying agent; one or more pH modifying agent; a humectant; a sweetening agent; a flavoring agent, and at least one vehicle.

Another embodiment disclosed herein relates to an oral liquid formulation comprising a therapeutically effective amount of methocarbamol; a suspending agent; a viscosity modifying agent; one or more pH modifying agent; a humectant; one or more pharmaceutically acceptable excipients, and at least one vehicle.

Yet another embodiment disclosed herein relates to an oral liquid formulation consisting of a therapeutically effective amount of methocarbamol; an antimicrobial agent; a suspending agent; a viscosity modifying agent; one or more pH modifying agent; a humectant; a sweetening agent; a flavoring agent, and at least one vehicle.

And yet another embodiment disclosed herein relates to an oral liquid formulation consisting essentially of a therapeutically effective amount of methocarbamol; an antimicrobial agent; a suspending agent; a viscosity modifying agent; one or more pH modifying agent; a humectant; one or more pharmaceutically acceptable excipients, and at least one vehicle.

Another embodiment disclosed herein relates to an oral liquid formulation comprising about 25 mg/mL to about 200 mg/mL methocarbamol; one or more pharmaceutically acceptable excipients, and at least one vehicle; wherein one or more pharmaceutically acceptable excipient is selected from group consisting of an antimicrobial agent; a suspending agent; a viscosity modifying agent; one or more pH modifying agent; a humectant; a sweetening agent, and a flavoring agent.

Yet another embodiment disclosed herein relates to an oral liquid formulation comprising about 2.5% w/w to about 20% w/w methocarbamol; one or more pharmaceutically acceptable excipients in an amount of from about 0.01% w/w to about 99% w/w, and at least one vehicle; wherein one or more pharmaceutically acceptable excipient is selected from group consisting of an antimicrobial agent; a suspending agent; a viscosity modifying agent; one or more pH modifying agent; a humectant; a sweetening agent, and a flavoring agent.

And yet another embodiment disclosed herein relates to an oral liquid formulation of methocarbamol comprising about 25 mg/mL to about 200 mg/mL methocarbamol; magnesium aluminum silicate as a suspending agent; sodium carboxymethylcellulose as a viscosity modifying agent; one or more pH modifying agent; glycerol as a humectant, and water as a vehicle.

Further, another embodiment of the oral liquid formulation relates to an oral liquid formulation comprising about 25 mg/mL to about 200 mg/mL methocarbamol; about 1 mg/mL to about 10 mg/mL magnesium aluminum silicate as a suspending agent; about 1 mg/mL to about 10 mg/mL sodium carboxymethylcellulose as a viscosity modifying agent; one or more pH modifying agent; about 100 mg/mL to about 400 mg/mL glycerol as a humectant, and water as a vehicle; wherein an oral liquid formulation has a pH from about 3 to about 6.

Yet another embodiment of the oral liquid formulation relates to an oral liquid formulation comprising about 1 mg/mL to about 500 mg/mL methocarbamol; about 0.01 mg/mL to about 20 mg/mL sodium benzoate as an antimicrobial agent; about 1 mg/mL to about 25 mg/mL magnesium aluminum silicate as a suspending agent; about 1 mg/mL to about 25 mg/mL sodium carboxymethylcellulose as a viscosity modifying agent; about 0.5 mg/mL to about 30 mg/mL trisodium citrate dihydrate as a pH modifying agent; about 0.5 mg/mL to about 30 mg/mL citric acid monohydrate as a pH modifying agent; about 1 mg/mL to about 700 mg/mL glycerol as a humectant; about 1 mg/mL to about 50 mg/mL sucralose as a sweetening agent; about 0.01 mg/mL to about 5 mg/mL tutti frutti flavor as a flavoring agent, and water as a vehicle.

Another embodiment relates to an oral liquid formulation comprising about 25 mg/mL to about 200 mg/mL methocarbamol; about 0.05 mg/mL to about 10 mg/mL sodium benzoate as an antimicrobial agent; about 1 mg/mL to about 10 mg/mL magnesium aluminum silicate as a suspending agent; about 1 mg/mL to about 10 mg/mL sodium carboxymethylcellulose as viscosity modifying agent; about 1 mg/mL to about 15 mg/mL trisodium citrate dihydrate as a pH modifying agent; about 1 mg/mL to about 20 mg/mL citric acid monohydrate as a pH modifying agent; about 100 mg/mL to about 400 mg/mL glycerol as humectant; about 10 mg/mL to about 25 mg/mL sucralose as sweetening agent; about 0.5 mg/mL to about 3 mg/mL tutti frutti flavor as a flavoring agent, and water as a vehicle.

Yet another embodiment relates to an oral liquid formulation comprising about 150 mg/mL methocarbamol; about 5 mg/mL sodium benzoate as an antimicrobial agent; about 4 mg/mL magnesium aluminum silicate as a suspending agent; about 5.4 mg/mL sodium carboxymethylcellulose as a viscosity modifying agent; about 5.37 mg/mL trisodium citrate dihydrate as a pH modifying agent; about 14.80 mg/mL citric acid monohydrate as a pH modifying agent; about 300 mg/mL glycerol as a humectant; about 19 mg/mL sucralose as a sweetening agent; about 2 mg/mL tutti frutti flavor as a flavoring agent, and water as a vehicle.

Another embodiment relates to a process for preparing the oral liquid formulation disclosed herein, which comprises:
mixing together methocarbamol; a suspending agent; a viscosity modifying agent; one or more pH modifying agent; a humectant, and water as a vehicle.

In one aspect, the process comprises adding of purified water in a stainless-steel vessel with stirring.

In yet another aspect, the process comprises adding a suspending agent and a viscosity modifying agent to form a uniform dispersion.

In yet another aspect, the process comprises adding one or more pH modifying agent, and a sweetening agent.

In yet another aspect, the process comprises adding a humectant.

In yet another aspect, the process comprises adding antimicrobial agent and a flavoring agent.

In one aspect, the process comprises adding methocarbamol.

In yet another aspect, the process further comprises homogenizing and observing the pH of the dispersion.

In another aspect, the process comprises adjusting the volume with purified water and stirring.

In yet another aspect, the process comprises filling the suspension in the suitable container (e.g., bottle).

In yet another aspect, the process comprises sealing and packing the suitable container (e.g., bottle).

Another main embodiment disclosed herein relates to a process for preparing an oral liquid formulation comprising:
a. Adding purified water in a stainless-steel vessel with stirring;
b. Adding suspending agent, and viscosity modifying agent in the solution of step (a) to form a uniform dispersion;
c. Decreasing the speed of the stirring;
d. Adding one or more pH modifying agent, and sweetening agent in the solution of step (c), and mixing with stirring for 30 minutes;
e. Adding humectant in the solution of step (d), and homogenizing it for 15 minutes;
f. Adding the antimicrobial agent, and flavoring agent sequentially in step (e), and homogenizing for 15 minutes;
g. Adding methocarbamol API in step (f), and mixing till get a dispersion medium;
h. Homogenizing the solution of step (g) for 60 minutes;
i. Observing the pH of the dispersion of step (h);
j. Adjusting the volume of the solution of step (i) with purified water, and stirring continuously for 20 minutes;
k. The final formulation of step (j) was stored in amber glass bottle, and CRC capping of bottle.

In one aspect of the oral liquid formulation, the oral liquid formulation has a viscosity in the range from about 50 cps to about 700 cps, and all values in between, such as from about 50 cps to about 500 cps, from about 100 cps to about 400 cps, and from about 100 cps to about 200 cps.

In one aspect, the oral liquid formulation can be selected from a solution or a suspension. In yet another aspect, the oral liquid formulation is in the form of a suspension.

According to one embodiment, an oral liquid formulation of methocarbamol is stable for 1 month, 3 months, and 6 months at 40° C.±2° C./75% RH or 25° C.±2° C./60% RH±5% RH or 30° C.±2° C./65% RH.

According to one embodiment, an oral liquid formulation of methocarbamol is stable for 1 month, 3 months, 6 months, 12 months, 18 months, 24 months or longer time at 40° C.±2° C./75% RH or 25° C.±2° C./60% RH±5% RH or 30° C.±2° C./65% RH.

According to one embodiment, an oral liquid formulation of methocarbamol is stable 40° C.±2° C./75% RH or 25° C.±2° C./60% RH±5% RH or 30° C.±2° C./65% RH for at least 6 months.

According to one embodiment, an oral liquid formulation disclosed herein has a total impurities less than 1.0% and any single unspecified impurities are less than 0.2% after 1 month, 3 months, and 6 months of storage at 40° C.±2° C./75% RH or 25° C.±2° C./60% RH±5% RH or 30° C.±2° C./65% RH.

In one aspect, the oral liquid formulation of methocarbamol when administered as a single dose to a subject under fasted condition provides a geometric least square ranges of pharmacokinetic profiles like maximum plasma concentration ($C_{max}$) from about 10000 ng/ml to about 20000 ng/ml; area under the plasma concentration versus time curve from time 0 to the last measurable concentration time ($AUC_{0-t}$) from about 25000 hr*ng/mL to about 40000 hr*ng/ml, and area under the plasma concentration versus time curve from time 0 to infinity ($AUC_{0-\infty}$) from about 25000 hr*ng/ml to about 40000 hr*ng/mL.

In yet another aspect, the oral liquid formulation of methocarbamol when administered as a single dose to a subject under fasted condition which provides a geometric least square ranges of pharmacokinetic profiles like maximum plasma concentration ($C_{max}$) 15024.64 ng/mL; area under the plasma concentration versus time curve from time 0 to the last measurable concentration time ($AUC_{0-t}$) 32827.15 hr*ng/mL, and area under the plasma concentration versus time curve from time 0 to infinity ($AUC_{0-\infty}$) 33224.25 hr*ng/mL.

In one aspect of the oral liquid formulation disclosed herein, the oral liquid formulation of methocarbamol, when administered as a single dose to a subject has a T/R ratio from 80% to 125%.

The oral liquid formulation disclosed herein is stable and provides better patient compliance.

Another embodiment relates to an oral liquid formulation disclosed herein useful for treatment of an adjunct to rest, physical therapy, and other measures for the relief of discomfort associated with acute, painful musculoskeletal conditions.

Yet another embodiment relates to a method for the treatment of, as adjunct to rest, physical therapy, and other measures for the relieve and discomfort associated with acute, painful musculoskeletal conditions in a patient in need thereof, wherein said method comprises administering a therapeutically effective amount of an oral liquid formulation disclosed herein.

And yet another embodiment relates to a package comprising an oral liquid formulation disclosed herein contained in a sealed bottle; and packaging material comprising written instructions for use.

Aspects of the oral liquid formulation disclosed herein is further illustrated by the following examples which are provided to be exemplary and do not limit the scope of the claimed oral liquid formulation.

EXAMPLES

Example 1: Solubility of Methocarbamol

Solubility of Methocarbamol was carried out in different vehicles at various pH conditions, and the results are presented in Table 1.

TABLE 1

Solubility of methocarbamol

| No. | Medium | Solubility (mg/ml) | Vol. req. to dissolve 1500 mg API (ml) |
| --- | --- | --- | --- |
| 1 | 0.1N HCl | 15.47 | 100.00 |
| 2 | pH 4.5 acetate buffer | 16.86 | 88.96 |
| 3 | pH 6.8 phosphate buffer | 14.10 | 106.38 |
| 4 | pH 7.2 phosphate buffer | 13.64 | 109.96 |
| 5 | Purified water | 15.30 | 98.02 |

Based on above data it can be concluded that Methocarbamol is having high solubility in all pH media. Therefore, purified water is finalized to be used as a vehicle.

Example 2: Drug-Excipients Compatibility Study

Primary selection of excipients was based on the excipients listed by the reference product (ROBAXIN Tablet) and on excipients used for oral suspension dosage form. Compatibility study was conducted to investigate and predict physico-chemical interactions between drug substance and excipients and to select the excipients during formulation development.

Method

Accurately weighed quantity of methocarbamol, and individual excipients were mixed as per ratio mentioned in the drug-excipient compatibility table. Mixtures were filled in glass vials, plugged using LDPE plugs which were manually punctured.

Filled glass vials were exposed to temperature and humidity conditions i.e. 60° C.±2° C., and 40° C.±2° C./75±5% RH for 4 weeks. The results of which are summarized in Table 2.

TABLE 2

Results of physical appearance for drug-excipient compatibility study

| No. | Description | Ratio | Initial | 60° C (4 weeks) | 40° C/75% RH (4 weeks) |
| --- | --- | --- | --- | --- | --- |
| 1. | Methocarbamol API dispersed in purified water at pH 4 (3-5) adjusted citric acid monohydrate & sodium citrate | 750 mg:0 mg | Off White dispersion | No Significant Change | No Significant Change |
| 2. | Methocarbamol API dispersed in purified water at pH 4 (3-5) adjusted with citric acid monohydrate & sodium citrate:glycerol | 750 mg:1000 mg | Off White dispersion | No Significant Change | No Significant Change |
| 3. | Methocarbamol API dispersed in purified water at pH 4 (3-5) adjusted with citric acid monohydrate & sodium citrate:sucralose | 750 mg:150 mg | Off White dispersion | No Significant Change | No Significant Change |
| 4. | Methocarbamol API dispersed in purified water at pH 4 (3-5) adjusted with citric acid monohydrate & sodium citrate:maltitol liquid | 750 mg:5000 mg | Off White dispersion | No Significant Change | No Significant Change |
| 5. | Methocarbamol API dispersed in purified water at pH 4 (3-5) adjusted with citric acid monohydrate & sodium citrate:sucrose | 750 mg:1500 mg | Off White dispersion | No Significant Change | No Significant Change |
| 6. | Methocarbamol API dispersed in purified water at pH 4 (3-5) adjusted with citric acid monohydrate & sodium citrate:carmellose sodium | 750 mg:20 mg | Off White dispersion | No Significant Change | No Significant Change |
| 7. | Methocarbamol API dispersed in purified water at Ph 4 (3-5) adjusted with citric acid monohydrate & sodium citrate:VEEGUM K | 750 mg:400 mg | Off White dispersion | No Significant Change | No Significant Change |
| 8. | Methocarbamol API dispersed in purified water at pH 4 (3-5) adjusted with citric acid | 750 mg:25 mg | Off White dispersion | No Significant Change | No Significant Change |

TABLE 2-continued

Results of physical appearance for drug-excipient compatibility study

| No. | Description | Ratio | Initial | 60° C (4 weeks) | 40° C/75% RH (4 weeks) |
|---|---|---|---|---|---|
| 9. | Methocarbamol API dispersed in purified water at pH 4 (3-5) adjusted with citric acid monohydrate & sodium citrate:sodium benzoate | 750 mg:10 mg | Off White dispersion | No Significant Change | No Significant Change |
| 10. | Methocarbamol API dispersed in purified water at pH 4 (3-5) adjusted with citric acid monohydrate & sodium citrate:sodium lauryl sulphate | 750 mg:10 mg | Off White dispersion | No Significant Change | No Significant Change |
| 11. | Methocarbamol API dispersed in purified water at pH 4 (3-5) adjusted with citric acid monohydrate & sodium citrate:methyl parahydroxy benzoate | 750 mg:20 mg | Off White dispersion | No Significant Change | No Significant Change |
| 12. | Methocarbamol API dispersed in purified water at pH 4 (3-5) adjusted with citric acid monohydrate & sodium citrate:lemon flavour | 750 mg:20 mg | Off White dispersion | No Significant Change | No Significant Change |
| 13. | Methocarbamol API dispersed in purified water at pH 4 (3-5) adjusted with citric acid monohydrate & sodium citrate:peppermint flavour | 750 mg:20 mg | Off White dispersion | No Significant Change | No Significant Change |
| 14. | Methocarbamol API dispersed in purified water at pH 4 (3-5) adjusted with citric acid monohydrate & sodium citrate:aspartame citrate:stearic acid | 750 mg:1125 mg | Off White dispersion | No Significant Change | No Significant Change |

TABLE 3

Results of related substance for drug excipient compatibility study

| Sample No. | Source of Impurity Specifications | Condition | Guaifenesin Process/ Degradation NMT 0.15% | Guaifenesin β isomer Process NMT 0.15% | Methocarbamol Isomer Process/ Degradation NMT 0.15% | Methocarbamol Dioxolone Process/ Degradation NMT 0.15% | Highest Unknown Impurity NMT 0.10% | Total Impurity NMT 1.0% |
|---|---|---|---|---|---|---|---|---|
| 1 | Methocarbamol API dispersed in purified water at pH 4 (3-5) adjusted with citric acid monohydrate & sodium citrate | Initial | 0.11% | 0.00% | 0.01% | 0.00% | 0.00% | 0.12% |
| | | 60° C. for 1 month | 1.27% | 0.00% | 0.73% | 1.37% | 0.03% | 3.40% |
| | | 40° C./75% RH for 1 month | 0.14% | 0.00% | 0.02% | 0.04% | 0.00% | 0.20% |
| 2 | Methocarbamol API dispersed in purified water at pH 4 (3-5) adjusted with citric acid monohydrate & sodium citrate: glycerol | Initial | 0.11% | 0.00% | 0.00% | 0.00% | 0.00% | 0.12% |
| | | 60° C. for 1 month | 1.14% | 0.00% | 1.07% | 0.95% | 0.00% | 3.16% |
| | | 40° C./75% RH for 1 month | 0.15% | 0.00% | 0.03% | 0.04% | 0.00% | 0.22% |
| 3 | Methocarbamol API dispersed in purified water at pH 4 (3-5) adjusted with citric acid monohydrate & sodium citrate: sucralose | Initial | 0.11% | 0.00% | 0.01% | 0.00% | 0.00% | 0.12% |
| | | 60° C. for 1 month | 0.12% | 0.00% | 0.02% | 0.01% | 0.00% | 0.15% |
| | | 40° C./75% RH for 1 month | 0.14% | 0.00% | 0.02% | 0.03% | 0.00% | 0.19% |
| 4 | Methocarbamol API dispersed in purified water at | Initial | 0.11% | 0.00% | 0.01% | 0.00% | 0.00% | 0.12% |
| | | 60° C. for 1 month | 0.27% | 0.00% | 0.82% | 0.17% | 0.01% | 1.27% |

TABLE 3-continued

Results of related substance for drug excipient compatibility study

| Sample No. | Source of Impurity Specifications | Condition | Guaifenesin Process/ Degradation NMT 0.15% | Guaifenesin β isomer Process NMT 0.15% | Methocarbamol Isomer Process/ Degradation NMT 0.15% | Methocarbamol Dioxolone Process/ Degradation NMT 0.15% | Highest Unknown Impurity NMT 0.10% | Total Impurity NMT 1.0% |
|---|---|---|---|---|---|---|---|---|
| | pH 4 (3-5) adjusted with citric acid monohydrate & sodium citrate: maltitol liquid | 40° C./75% RH for 1 month | 0.11% | 0.00% | 0.03% | 0.01% | 0.00% | 0.15% |
| 5 | Methocarbamol API dispersed in purified water at pH 4 (3-5) adjusted with citric acid monohydrate & sodium citrate: sucrose | Initial | 0.12% | 0.00% | 0.01% | 0.00% | 0.00% | 0.13% |
| | | 60° C. for 1 month | 0.75% | 0.02% | 0.68% | 0.92% | 0.12% | 2.67% |
| | | 40° C./75% RH for 1 month | 0.13% | 0.00% | 0.02% | 0.03% | 0.00% | 0.19% |
| 6 | Methocarbamol API dispersed in purified water at pH 4 (3-5) adjusted with citric acid monohydrate & sodium citrate: carmellose sodium | Initial | 0.11% | 0.00% | 0.01% | 0.00% | 0.04% | 0.16% |
| | | 60° C. for 1 month | 1.37% | 0.01% | 0.84% | 1.38% | 0.00% | 3.61% |
| | | 40° C./75% RH for 1 month | 0.15% | 0.00% | 0.02% | 0.04% | 0.00% | 0.21% |
| 7 | Methocarbamol API dispersed in purified water at pH 4 (3-5) adjusted with citric acid monohydrate & sodium citrate: VEEGUM K (Magnesium Aluminum Silicate) | Initial | 0.11% | 0.00% | 0.02% | 0.00% | 0.09% | 0.23% |
| | | 60° C. for 1 month | 1.52% | 0.02% | 3.22% | 1.51% | 0.02% | 6.29% |
| | | 40° C./75% RH for 1 month | 0.14% | 0.01% | 0.06% | 0.08% | 0.09% | 0.39% |
| 8 | Methocarbamol API dispersed in purified water at pH 4 (3-5) adjusted with citric acid monohydrate & sodium citrate: sodium benzoate | Initial | 0.11% | 0.00% | 0.01% | 0.00% | 0.01% | 0.14% |
| | | 60° C. for 1 month | 1.46% | 0.01% | 0.77% | 1.51% | 0.00% | 3.76% |
| | | 40° C./75% RH for 1 month | 0.16% | 0.00% | 0.02% | 0.05% | 0.01% | 0.24% |
| 9 | Methocarbamol API dispersed in purified water at pH 4 (3-5) adjusted with citric acid monohydrate & sodium citrate: sodium lauryl sulphate | Initial | 0.11% | 0.00% | 0.01% | 0.01% | 0.03% | 0.16% |
| | | 60° C. for 1 month | 1.03% | 0.00% | 0.66% | 1.27% | 0.00% | 2.97% |
| | | 40° C./75% RH for 1 month | 0.15% | 0.00% | 0.02% | 0.05% | 0.00% | 0.22% |
| 10 | Methocarbamol API dispersed in purified water at pH 4 (3-5) adjusted with citric acid monohydrate & sodium citrate: methyl parahydroxy benzoate | Initial | 0.11% | 0.00% | 0.01% | 0.01% | 0.00% | 0.13% |
| | | 60° C. for 1 month | 0.88% | 0.00% | 0.53% | 1.11% | 0.00% | 2.52% |
| | | 40° C./75% RH for 1 month | 0.15% | 0.00% | 0.02% | 0.04% | 0.00% | 0.22% |
| 11 | Methocarbamol API dispersed in purified water at | Initial | 0.11% | 0.00% | 0.01% | 0.00% | 0.00% | 0.13% |
| | | 60° C. for 1 month | 0.78% | 0.00% | 0.53% | 0.95% | 0.00% | 2.26% |

TABLE 3-continued

Results of related substance for drug excipient compatibility study

| No. | Sample Source of Impurity Specifications | Condition | Guaifenesin Process/ Degradation NMT 0.15% | Guaifenesin β isomer Process NMT 0.15% | Methocarbamol Isomer Process/ Degradation NMT 0.15% | Methocarbamol Dioxolone Process/ Degradation NMT 0.15% | Highest Unknown Impurity NMT 0.10% | Total Impurity NMT 1.0% |
|---|---|---|---|---|---|---|---|---|
| | pH 4 (3-5) adjusted with citric acid monohydrate & sodium citrate: lemon flavour | 40° C./75% RH for 1 month | 0.15% | 0.00% | 0.02% | 0.04% | 0.00% | 0.20% |
| 12 | Methocarbamol API dispersed in purified water at | Initial | 0.11% | 0.00% | 0.01% | 0.00% | 0.00% | 0.12% |
| | | 60° C. for 1 month | 1.20% | 0.00% | 0.76% | 1.29% | 0.01% | 3.27% |
| | pH 4 (3-5) adjusted with citric acid monohydrate & sodium citrate: peppermint flavour | 40° C./75% RH for 1 month | 0.15% | 0.00% | 0.02% | 0.04% | 0.00% | 0.21% |
| 13 | Methocarbamol API dispersed in purified water at | Initial | 0.11% | 0.00% | 0.01% | 0.01% | 0.00% | 0.13% |
| | | 60° C. for 1 month | 0.92% | 0.00% | 0.53% | 1.11% | 0.01% | 2.58% |
| | pH 4 (3-5) adjusted with citric acid monohydrate & sodium citrate: aspartame | 40° C./75% RH for 1 month | 0.14% | 0.00% | 0.02% | 0.04% | 0.02% | 0.23% |
| 14 | Methocarbamol API dispersed in Purified Water at | Initial | 0.03% | 0.00% | 0.00% | 0.00% | 0.00% | 0.03% |
| | | 60° C. for 1 month | 0.43% | 0.00% | 0.11% | 0.82% | 0.00% | 1.36% |
| | pH 4 (3-5) adjusted with Citric Acid Monohydrate & Sodium Citrate: Stearic Acid | 40° C./75% RH for 1 month | 0.03% | 0.00% | 0.01% | 0.01% | 0.00% | 0.05% |

NMT: Not More Than;
RH: Relative Humidity

Based on above data, it was observed that in presence of aqueous media guaifenesin impurity was observed to be increased up to 0.11% level at initial itself, which further crossed 0.15% level when stored at 60° C. temperature condition. At 60° C. temperature condition all impurity levels (except unknown impurity) were observed to be higher in almost all drug: excipient combinations. This indicates probable instability of methocarbamol in aqueous phase at higher temperature conditions.

After 1 month storage at 40° C./75% RH condition, slight increase in guaifenesin impurity from initial level was observed for all API/excipient combinations. API/aluminum magnesium silicate combination also showed rise in levels of methocarbamol isomer & Methocarbamol dioxolone impurities (above 0.05%) after 1 month storage at 40° C./75% RH condition.

Example 3: Formulation of Oral Liquid Suspension Methocarbamol (CRL-007-039)

TABLE 4

Formulation of oral liquid suspension of methocarbamol

| No. | Material | Qty/Unit mg/ml | Qty/Unit mg/5 ml |
|---|---|---|---|
| 1 | Methocarbamol | 150.00 | 750.00 |
| 2 | Sodium benzoate | 5.00 | 25.00 |
| 3 | Glycerol | 300.00 | 1500.00 |
| 4 | Aluminum magnesium silicate | 6.00 | 30 |
| 5 | Colloidal silicon dioxide | 20.00 | 100.00 |
| 6 | Citric acid monohydrate | 11.60 | 58.02 |
| 7 | Sodium citrate (Trisodium citrate dihydrate) | 5.366 | 26.83 |
| 8 | Sucralose | 19.00 | 95.00 |
| 9 | Tutti-fruity flavor | 2.00 | 10.00 |
| 10 | Purified water | Q.S. | Q.S. |

Q.S.: Quantity Sufficient

Procedure:
(a) The buffering agents was dissolved in purified water and mixed with continuous stirring for 30 minutes;
(b) The preservative was added to the solution of step (a) and mixed with continuous stirring for 30 minutes;
(c) The suspending and thickening agents were dissolved to solution of step (b) and mixed with continuous stirring for 180 minutes;
(d) The humectant was added to solution of step (c) and mixed with continuous stirring for 30 minutes;
(e) The sweetening agent was added to solution of step (d) and mixed with continuous stirring for 10 minutes;
(f) The methocarbamol was added to solution of step (e) and mixed with continuous stirring for 60 minutes;
(g) The flavouring agent was added to solution of step (f) and mixed with continuous stirring for 10 minutes;
(h) The formulated dispersion of step (g) was homogenized for 30 minutes;
(i) The final formulation of step (h) was stored in amber glass bottle & child resistant closure (CRC) capping of bottle.

Example 4: Comparative Evaluation of ROBAXIN-750 Tablets and Methocarbamol 750 Mg/5 ML Oral Suspension

TABLE 5

Comparative evaluation of ROBAXIN-750 tablets and methocarbamol 750 mg/5 ml oral suspension

| No. | Parameter | ROBAXIN-750 | | Methocarbamol 750 mg/5 ml Oral Suspension | |
|---|---|---|---|---|---|
| 1 | Description | White to off white, capsule shaped film coated tablets having score-line on one side and embossed with '3009' on another side. | | White to off white liquid suspension free from lumps and coagulated mass. | |
| 2 | Dosage Form | Tablet | | Oral Suspension | |
| 3 | Batch No. | 14LA | | CRL-007-039 | |
| 4 | Assay of Methocarbamol | 99.6% | | 103.9% | |
| 5 | Preservative Content | NA | | 99.4% | |
| 6 | pH | 3.42 (2 tablets/10 ml purified water) | | 4.60 | |
| 7 | Related Substances | Guaifenesin | 0.00% | Guaifenesin | 0.03% |
| | | β isomer | 0.00% | β isomer | Not Detected |
| | | Methocarbamol isomer | Not Detected | Methocarbamol isomer | 0.00% |
| | | Methocarbamol Dioxolone | Not Detected | Methocarbamol Dioxolone | Not Detected |
| | | Highest unknown impurity | 0.00% | Highest unknown impurity | 0.01% |
| | | Total impurities | 0.00% | Total impurities | 0.04% |

Example 5: Comparative Dissolution Study of Methocarbamol 750 MG/5 ML Oral Suspension (#CRL-007-039) Vs ROBAXIN-750 Mg Tablet (#14LA)

The dissolution condition of methocarbamol tablets USP was adopted.

TABLE 6

| Dissolution conditions | |
|---|---|
| Dissolution medium | Purified water/0.1N HCl/0.1N HCl (PEAK Vessel)/pH 4.5 acetate buffer/pH 4.5 acetate buffer (PEAK Vessel)/pH 6.8 phosphate buffer/pH 6.8 phosphate buffer (PEAK vessel) |
| Apparatus | 900 ml |
| Volume | Paddle (USP Type II) |
| Speed | 50 RPM |
| Recommended Sampling Time points (Minutes) | 5, 10, 15, 30, 45, 60 minutes |

USP: United States Pharmacopeia;
RPM: Rotates Per Minutes

TABLE 7

% Drug release in purified water

| Product | 5 min | 10 min | 15 min | 30 min | 45 min | 60 min | F2 |
|---|---|---|---|---|---|---|---|
| ROBAXIN 750 mg Tablet | 16% | 77% | 93% | 101% | 101% | 101% | Both Test & Reference product were releasing more than 85% within 15 minutes |
| Methocarbamol 750 mg/5 ml Oral Suspension | 102% | 102% | 103% | 103% | 103% | 103% | |

It was observed that the product was completely released within 15 minutes. So, it can be concluded that, oral suspension formulation (CRL-007-039) is also fast releasing similar to tablet formulation.

TABLE 8

% Drug Release in 0.1N HCL and 0.1N HCL (PEAK Vessel)

% Drug Release (Average) in 0.1N HCL

| Product | 5 min | 10 min | 15 min | 30 min | 45 min | 60 min | F2 |
|---|---|---|---|---|---|---|---|
| ROBAXIN 750 mg Tablet | 13% | 63% | 76% | 92% | 97% | 99% | F2 less than 50 |
| Methocarbamol 750 mg/5 ml Oral Suspension | 99% | 99% | 99% | 99% | 99% | 100% | |

% Drug Release (Average) in .1N HCL (PEAK Vessel)

| Product | 5 min | 10 min | 15 min | 30 min | 45 min | 60 min | F2 |
|---|---|---|---|---|---|---|---|
| ROBAXIN 750 mg Tablet | 28% | 87% | 96% | 100% | 100% | 101% | Both Test & Reference product were releasing more than 85% within 15 minutes |
| Methocarbamol 750 mg/5 ml Oral Suspension | 99% | 99% | 99% | 99% | 99% | 100% | |

Initially, heap formation in dissolution vessel was observed for ROBAXIN tablets. Due to which dissolution rate was slower. So, it was decided to perform dissolution with using PEAK Vessel. It was observed that the product was completely released within 15 minutes. So, it can be concluded that, oral suspension formulation (CRL-007-039) is also fast releasing similar to tablet formulation.

TABLE 9

% Drug release in pH 4.5 acetate buffer and pH 4.5 acetate buffer (PEAK Vessel)

% Drug Release (Average) in pH 4.5 acetate buffer

| Product | 5 min | 10 min | 15 min | 30 min | 45 min | 60 min | F2 |
|---|---|---|---|---|---|---|---|
| ROBAXIN 750 mg Tablet | 5% | 18% | 35% | 79% | 97% | 99% | Less than 50 |
| Methocarbamol 750 mg/5 ml Oral Suspension | 96% | 96% | 97% | 97% | 97% | 97% | |

% Drug Release (Average) in pH 4.5 acetate buffer (PEAK Vessel)

| Product | 5 min | 10 min | 15 min | 30 min | 45 min | 60 min | F2 |
|---|---|---|---|---|---|---|---|
| ROBAXIN 750 mg Tablet | 8% | 27% | 47% | 100% | 101% | 103% | Less than 50 |
| Methocarbamol 750 mg/5 ml Oral Suspension | 96% | 96% | 97% | 97% | 97% | 97% | |

Initially, heap formation in dissolution vessel was observed for ROBAXIN tablets. Due to which dissolution rate was slower. So, it was decided to perform dissolution with using PEAK vessel. Dissolution profile of oral suspension formulation (CRL-007-039) was found to be faster than ROBAXIN, till 15 minutes time point. However, observed to be releasing completely at 30 minutes time point.

TABLE 10

% Drug release in pH 6.8 phosphate buffer and pH 6.8 phosphate buffer (PEAK Vessel)

| Product | % Drug release (Average) in pH 6.8 phosphate buffer | | | | | | F2 |
|---|---|---|---|---|---|---|---|
| | 5 min | 10 min | 15 min | 30 min | 45 min | 60 min | |
| ROBAXIN 750 mg Tablet | 4 | 15 | 28 | 67 | 91 | 98 | Less than 50 |
| Methocarbamol 750 mg/5 ml Oral Suspension | 98 | 99 | 99 | 99 | 99 | 99 | |

| Product | % Drug release (Average) in pH 6.8 phosphate buffer (PEAK vessel) | | | | | | F2 |
|---|---|---|---|---|---|---|---|
| | 5 min | 10 min | 15 min | 30 min | 45 min | 60 min | |
| ROBAXIN 750 mg Tablet | 6 | 22 | 39 | 96 | 102 | 103 | Less than 50 |
| Methocarbamol 750 mg/5 ml Oral Suspension | 98 | 99 | 99 | 99 | 99 | 99 | |

Initially, heap formation in dissolution vessel was observed for ROBAXIN tablets. Due to which dissolution rate was slower. To confirm slower release profile of ROBAXIN is only due to heap formation, it was decided to perform dissolution studies in peak vessels. Dissolution profile of oral suspension formulation (CRL-007-039) was found to be faster than ROBAXIN, till 15 minutes time point. However, observed to be releasing completely at 30 minutes time point.

From the results of in-vitro dissolution data, it is observed that in 0.1 N HCL, both the products were releasing completely i.e. (Reference: 96%; Test: 99% within 15 minutes). From dissolution data it can be concluded that after oral administration both suspension and tablet, it will get dissolved completely in stomach (pH 1.2) environment before its transit to the intestine. Dissolution in pH 4.5 & 6.8 will not have significance for absorption as complete dissolution is reached before gastric emptying.

Example 6: Stability Data of Oral Liquid Formulation of Methocarbamol (CRL-007-039)

The stability study was conducted for 3 and 6 months at 40° C./75% RH & 25° C./60% RH.

TABLE 11

Stability study data of oral liquid formulation of methocarbamol (CRL-007-039)

| Parameter | | Specification | Stability Tests | | | | |
|---|---|---|---|---|---|---|---|
| | | | | 40° C./75% RH | | 25° C./60% RH | |
| | | | Initial | (3 M) | (6 M) | (3 M) | (6 M) |
| Assay of Methocarbamol | | 95-105% | 99.3% | 97.6% | 98.8% | 96.7% | 99.8% |
| Sodium Benzoate Content | | 80% 120% | 96.6% | 96.5% | 96.7% | 95.5% | 97.6% |
| pH | | 3.5-4.5 | 4.07 | 3.95 | | 3.90 | |
| Specific Gravity | | 1.10 ± 1.0 | 1.14 | 1.12 | | 1.10 | |
| Viscosity | | NLT 25 cps | 25.86 | 40.50 | | 28.80 | |
| Related Substances | Guaifenesin | 0.15% | 0.06% | 0.04% | 0.12% | 0.03% | 0.03% |
| | Guaifenesin β isomer | 0.15% | ND | ND | ND | ND | ND |
| | methocarbamol isomer | 0.15% | 0.02% | 0.01% | 0.05% | ND | ND |
| | Methocarbamol dioxolone | 0.15% | 0.03% | 0.02% | 0.04% | ND | ND |
| | Highest unknown impurity | 0.10% | ND | ND | ND | ND | ND |
| | Total impurities | 1.0% | 0.12% | 0.06% | 0.21% | 0.03% | 0.03% |
| Dissolution Test | | (Purified Water, Apparatus Type II, 900 ml, at 50 RPM) | | | | | |
| | 5 min | | 99 | 97 | 99 | 97 | 99 |
| | 10 min | | 100 | 98 | 100 | 98 | 100 |

TABLE 11-continued

Stability study data of oral liquid formulation of methocarbamol (CRL-007-039)

| Parameter | Specification | Stability Tests | | | | |
|---|---|---|---|---|---|---|
| | | | 40° C./75% RH | | 25° C./60% RH | |
| | | Initial | (3 M) | (6 M) | (3 M) | (6 M) |
| | 15 min | 100 | 98 | 101 | 98 | 100 |
| | 30 min | 100 | 98 | 101 | 98 | 100 |
| | 45 min | 100 | 98 | 101 | 98 | 101 |
| | 60 min | 100 | 98 | 101 | 98 | 101 |

M: Months;
ND: Not Detected;
RPM: Rotates Per Minutes;
CPS: Centipoise;
NLT: Not Less Than;
RH: Relative Humidity The optimized formulation was found to be stable at 40° C./75% RH & 25° C./60% RH up to 6 Months.

Example 7: Formulation of Oral Liquid Methocarbamol (B1)

TABLE 12

Formulation of oral liquid suspension of methocarbamol (B1)

| No. | Name of Material | Quantity/Unit mg/ml |
|---|---|---|
| 1 | Methocarbamol | 1-500 |
| 2 | Sodium benzoate | 0.01-20 |
| 3 | Glycerol | 1-700 |
| 4 | Magnesium aluminum silicate | 1-25 |
| 5 | Sodium carboxymethylcellulose | 1-25 |
| 6 | Citric acid monohydrate | 0.5-30 |
| 7 | Trisodium citrate dihydrate | 0.5-30 |
| 8 | Sucralose | 1-50 |
| 9 | Tutti-fruity flavor | 0.01-5 |
| 10 | Purified water | Q.S. |

Q.S.: Quantity Sufficient

Example 8: Formulation of Oral Liquid Suspension of Methocarbamol (B2)

TABLE 13

Formulation of oral liquid suspension of methocarbamol (B2)

| No. | Name of Material | Qty/Unit mg/ml |
|---|---|---|
| 1 | Methocarbamol | 25-200 |
| 2 | Sodium benzoate | 0.05-10 |
| 3 | Glycerol | 100-400 |
| 4 | Magnesium aluminum silicate | 1-10 |
| 5 | Sodium carboxymethylcellulose | 1-10 |
| 6 | Citric acid monohydrate | 1-20 |
| 7 | Trisodium citrate dihydrate | 1-15 |
| 8 | Sucralose | 10-25 |
| 9 | Tutti-fruity flavor | 0.5-3 |
| 10 | Purified water | Q.S. |

Q.S.: Quantity Sufficient

Example 9: Formulation of Oral Liquid Suspension of Suspension of Methocarbamol (B3)

TABLE 14

Formulation of oral liquid suspension of methocarbamol (B3)

| No. | Name of Material | Quantity/Unit mg/ml | Quantity/Unit mg/5 ml | Quantity/Unit % w/v |
|---|---|---|---|---|
| 1 | Methocarbamol | 150.00 | 750.00 | 15 |
| 2 | Sodium benzoate | 5.00 | 25.00 | 0.5 |
| 3 | Glycerol | 300.00 | 1500.00 | 30 |
| 4 | Magnesium aluminum silicate | 4.00 | 20.00 | 0.4 |
| 5 | Sodium carboxymethylcellulose | 5.4 | 27.00 | 0.54 |
| 6 | Citric acid monohydrate | 14.804 | 74.02 | 1.480 |
| 7 | Trisodium citrate dihydrate | 5.366 | 26.83 | 0.536 |
| 8 | Sucralose | 19.00 | 95.00 | 1.9 |
| 9 | Tutti-fruity flavor | 2.00 | 10.00 | 0.2 |
| 10 | Purified water | Q.S. | Q.S. | Q.S. |

Q.S.: Quantity Sufficient

Procedure:
(a) The purified water was added in a stainless-steel vessel with stirring;
(b) The magnesium aluminum silicate and sodium carboxymethylcellulose were added in the solution of step (a) to form a uniform dispersion;
(c) The speed of the stirring was decreased;
(d) Trisodium citrate dihydrate, citric acid monohydrate and sucralose were added
in the solution of step (c) and mixing with stirring for 30 minutes;
(e) The glycerol was added in the solution of step (d) and homogenized it for 15 minutes;
(f) The sodium benzoate and Tutti Frutti flavor were added sequentially in step (e) and homogenizing for 15 minutes;
(g) The methocarbamol API was added in step (f) and mixed till get a dispersion medium;
(h) Homogenized the solution of step (g) for 60 minutes;
(i) Observed the pH of the dispersion if step (h);
(j) Adjusted the volume of the solution of step (i) with purified water and stirred continuously for 20 minutes;
(k) The final formulation of step (j) was stored in amber glass bottle & CRC capping of bottle.

Example 10: Comparative Evaluation of Methocarbamol 750 MG/5 ML with ORTOTON® Recordati 750 MG Film Coated Tablets and ROBAXIN®-750 Film Coated Tablet

TABLE 15

Comparative evaluation of methocarbamol 750 mg/5 ml with ORTOTON ® Recordati 750 mg film coated tablets and ROBAXIN ®-750 film coated tablet

| No. | Physical & chemical Parameters | ORTOTON ® Recordati 750 mg Film coated tablets | ROBAXIN ®-750 film coated Tablets | Formulation B3 (750 mg/5 ml) |
|---|---|---|---|---|
| 1. | Description | White, slightly convex, oblong film-coated tablets with a score line on both sides | White to off white, capsule shaped film coated tablets having score-line on one side and embossed with '3009' on another side. | Off white, viscous oral suspension. |
| 2. | pH | Not applicable | Not applicable | 3.68 |
| 3. | Viscosity | Not applicable | Not applicable | 610.5 cps |
| 4. | Assay (%) | 98.0% | 99.6% | 99.6% |
| 5. | Specific gravity | Not applicable | Not applicable | 1.1318 |
| 6. | Preservative content (Sodium benzoate) | Not applicable | Not applicable | 96.6% |
| 7. | Related Substances | | | |
| | Guaifenesin | 0.03% | 0.002% | ND |
| | Guaifenesin β-Isomer | ND | 0.001% | 0.01% |
| | Methocarbamol Isomer | 0.01% | ND | 0.01% |
| | Methocarbamol Dioxolone | ND | ND | ND |
| | Single maximum unknown impurity | ND | 0.00% | 0.00% |
| | Total Impurity | 0.04% | 0.003% | 0.02% |
| 8. | Dissolution Study: Media: Purified Water, Volume: 900 ml, Apparatus: Paddle; Speed: 50 RPM | | | |

| Time points (Min.) | % Drug released | % RSD | % Drug released | % RSD | % Drug released | % RSD |
|---|---|---|---|---|---|---|
| 5 | 30 | 17.32 | 16 | 9.67 | 23 | 5.08 |
| 10 | 78 | 7.13 | 77 | 9.64 | 30 | 4.55 |
| 15 | 91 | 3.01 | 93 | 5.16 | 43 | 2.30 |
| 30 | 99 | 0.88 | 101 | 0.94 | 65 | 4.61 |
| 45 | 100 | 0.60 | 101 | 0.78 | 90 | 3.72 |
| 60 | 101 | 0.65 | 101 | 1.09 | 96 | 1.02 |

ND: Not Detected;
RPM: Rotates Per Minutes;
CPS: Centipoise;
RSD: Relative Standard Deviation The results indicates that all physical and chemical parameters were found satisfactory. Also, dissolution profile of formulation B3 was found similar with marketed formulations.

Example 11: Stability Data of Formulation B3

The stability study was conducted for 3 and 6 months at 40° C./75% RH & 25° C./60% RH, the results of which are summarized in Table 16.

TABLE 16

Stability study data of formulation B3

| Parameters | Specification | Initial | 40° C./ 75% RH 1 M | 40° C./ 75% RH 3 M | 40° C./ 75% RH 6 M | 25° C./ 60% RH 3 M | 25° C./ 60% RH 6 M | 30° C./ 65% RH 6 M |
|---|---|---|---|---|---|---|---|---|
| Description | Off white, viscous oral suspension. | | Off white, viscous oral suspension. | | | | | |
| Assay (%) | 95-105% | 99.6% | 100.2% | 100.1% | 100.4% | 99.3% | 100.7% | 100.8% |
| pH | 3.2-4.8 | 3.68 | 3.85 | 3.88 | 3.91 | 3.85 | 3.92 | 3.94 |

TABLE 16-continued

Stability study data of formulation B3

| | | | | | | | | |
|---|---|---|---|---|---|---|---|---|
| Sodium Benzoate Content | 80-120% | 24.15 mg/5 ml | 24.351 mg/5 ml | 23.509 mg/5 ml | 23.93 mg/5 ml | 23.755 mg/5 ml | 23.35 mg/5 ml | 23.31 mg/5 ml |
| Specific Gravity | 1.100 ± 0.1 | 1.1318 | 1.1322 | 1.1285 | 1.1274 | 1.1253 | 1.1275 | 1.1311 |

Related Substances

| | | | | | | | | |
|---|---|---|---|---|---|---|---|---|
| Guaifenesin | 0.15% | 0.01% | 0.02% | 0.04% | 0.08% | 0.01% | 0.01% | 0.02% |
| β-isomer | 0.15% | ND | ND | ND | ND | ND | ND | ND |
| Dioxolone | 0.15% | ND | ND | ND | ND | ND | ND | ND |
| Methocarbamol Isomer | 0.15% | 0.01% | 0.01% | 0.02% | 0.03% | 0.01% | 0.01% | 0.01% |
| Highest Unknown Impurity | 0.10% | 0.00% | 0.01% | 0.03% | 0.03% | 0.00% | 0.00% | 0.01% |
| Total Impurities | 1.0% | 0.02% | 0.04% | 0.09% | 0.14% | 0.02% | 0.02% | 0.04% |

Dissolution
Purified Water, 900 ml, Paddle 50 RPM

| Time points (Min.) | | % release | % release | % release | % release | % release | % release | % release |
|---|---|---|---|---|---|---|---|---|
| 10 | NLT 75% (Q) | 30 | 33 | 55 | 75 | 36 | 38 | 68 |
| 15 | of the labeled | 43 | 49 | 68 | 83 | 49 | 50 | 83 |
| 30 | amount of | 65 | 74 | 86 | 93 | 80 | 79 | 96 |
| 45 | Methocarbamol | 90 | 87 | 94 | 99 | 95 | 98 | 99 |
| 60 | dissolved in 45 minutes | 96 | 96 | 98 | 101 | 99 | 99 | 101 |

ND: Not Detected;
RPM: Rotates Per Minutes;
NLT: Not Less Than;
Q: Quantity;
M: Months;
RH: Relative Humidity The results indicates that the final formulation was found to be stable at 40° C./75% RH & 25° C./60% RH up to 6 Months.

Example 12: Photo Stability Study

A. Photostability Study Procedure:

Photostability study was performed on the formulation B3 as summarized in Table 17.

TABLE 17

Results of photostability study

| | | | Methocarbamol API (Batch no: A) | | | Finished product (Formulation-B3) | | | |
|---|---|---|---|---|---|---|---|---|---|
| No. | Test parameters | Stability Product Specification | Initial | API in open Exposed Condition | API in Protected Condition (Control) | Initial | Open exposed drug product outside of the immediate pack | Drug product in the immediate (primary pack) | Protected samples (e.g. wrapped in aluminum foil) are used as dark controls |
| 1. | Description | Off white, viscous oral suspension. | White Bulky Powder odorless | | | Off white, viscous oral suspension. | | | |
| 2. | Viscosity (cps) | NLT 400 cps | — | — | — | 610.5 | 546.0 | 591.0 | 603.0 |
| 3. | pH | 3.2-4.8 | — | — | — | 3.73 | 3.87 | 3.84 | 3.82 |
| 4. | Specific Gravity | 1.100 ± 0.1 | — | — | — | 1.1319 | 1.1347 | 1.1340 | 1.1386 |
| 5. | Assay (%) | 95-105% | 99.3% | 99.8% | 99.2% | 101.2% | 103.2% | 103.4% | 102.6% |
| 6. | Sodium Benzoate Content (%) | 80-120% | — | — | — | 98.1% | 101.3% | 99.5% | 100.8% |

TABLE 17-continued

Results of photostability study

| | | | Methocarbamol API (Batch no: A) | | | Finished product (Formulation-B3) | | | |
|---|---|---|---|---|---|---|---|---|---|
| No. | Test parameters | Stability Product Specification | Initial | API in open Exposed Condition | API in Protected Condition (Control) | Initial | Open exposed drug product outside of the immediate pack | Drug product in the immediate (primary pack) | Protected samples (e.g. wrapped in aluminum foil) are used as dark controls) |
| 7. | | | | Related Substances | | | | | |
| i | β-Isomer | 0.15% | ND | ND | ND | ND | ND | ND | ND |
| ii | Guaifenesin | 0.15% | 0.03% | 0.01% | 0.01% | 0.01% | 0.01% | 0.01% | 0.01% |
| iii | Methocarbamol Isomer | 0.15% | ND | 0.02% | 0.01% | 0.01% | 0.01% | 0.01% | 0.01% |
| iv | Dioxolone | 0.15% | ND | ND | ND | ND | ND | ND | ND |
| v | Highest Unknown Impurity | 0.10% | ND | ND | ND | 0.00% | 0.01% | 0.00% | 0.00% |
| vi | Total Impurities | 1.0% | 0.03% | 0.03% | 0.02% | 0.02% | 0.03% | 0.02% | 0.02% |
| 8. | Dissolution Profile | | | | | | | | |

Media-Purified Water; Media Volume-900 ml at 37° C.; Apparatus-2 (Paddle); Speed-50 RPM; Time Points-5, 10, 15, 30, 45, 60

| N = 6 Units Time points (In Minutes) | | | | | % Drug Released (% RSD) | % Drug Released (% RSD) | % Drug Released (% RSD) | % Drug Released (% RSD) |
|---|---|---|---|---|---|---|---|---|
| 5 | — | — | — | — | 17 (6.55) | 25 (11.85) | 20 (11.89) | 18 (4.79) |
| 10 | — | — | — | — | 29 (6.44) | 41 (9.97) | 33 (7.19) | 30 (4.78) |
| 15 | — | — | — | — | 42 (3.89) | 55 (8.28) | 44 (5.63) | 43 (5.30) |
| 30 | — | — | — | — | 68 (2.89) | 81 (6.76) | 74 (2.62) | 71 (4.44) |
| 45 | — | — | — | — | 88 (3.28) | 93 (5.56) | 89 (2.06) | 87 (3.74) |
| 60 | — | — | — | — | 95 (3.45) | 98 (4.38) | 100 (1.01) | 99 (3.33) |

ND: Not Detected;
RPM: Rotates Per Minutes;
CPS: Centipoise;
RSD: Relative Standard Deviation;
NLT: Not Less Than The results indicates that the final formulation was found to be stable at Photostability condition.

Example 13: Freeze Thaw Study

TABLE 18

Freeze thaw study details

| No. | Batch No. | Condition | Cycle |
|---|---|---|---|
| 1 | Formulation B3 | Upright ↑ | 3 |

Testing condition
Step 1: Freezer (−20° C.) for 48 Hrs.
Step 2: Accelerated temperature (40° C./75% RH) for 48 Hrs.

TABLE 19

Results of freeze-thaw study

| | B. No Formulation B3 Condition | |
|---|---|---|
| | INITIAL | Freeze thaw stability after 3 cycles |
| Methocarbamol 750 mg/5 ml Oral Suspension | | |
| Description | Off white, viscous oral suspension. | Off white, viscous oral suspension. |
| Viscosity | 610.5 cps | 633.0 cps |
| pH | 3.73 | 3.86 |
| Specific Gravity | 1.1319 | 1.1359 |
| Methocarbamol Assay | 101.2% | 103.1% |
| Sodium Benzoate | 98.1% | 99.9% |
| Related Substances | | |
| β-Isomer | ND | ND |
| Guaifenesin | 0.01% | 0.01% |

TABLE 19-continued

Results of freeze-thaw study

| | | |
|---|---|---|
| Methocarbamol Isomer | 0.01% | 0.01% |
| Dioxolone | ND | ND |
| Highest Unknown Impurity | 0.00% | 0.00% |
| Total Impurities | 0.02% | 0.02% |
| Dissolution Profile N = 6 Units | Media- Purified Water; Media Volume- 900 ml at 37° C.; Apparatus - 2 (Paddle); Speed - 50 RPM; Time Points - 5, 10, 15, 30, 45, 60 | |

| Time (In Minutes) | % Drug Released | % RSD | % Drug Released | % RSD |
|---|---|---|---|---|
| 5 | 17 | 6.55 | 14 | 8.02 |
| 10 | 29 | 6.44 | 26 | 3.94 |
| 15 | 42 | 3.89 | 37 | 2.97 |
| 30 | 68 | 2.89 | 62 | 2.49 |
| 45 | 88 | 3.28 | 76 | 3.07 |
| 60 | 95 | 3.45 | 86 | 4.06 |

ND: Not Detected;
RPM: Rotates Per Minutes;
CPS: Centipoise;
RSD: Relative Standard Deviation;
NLT: Not Less Than The results indicates that the final formulation was found to be stable at freeze thaw condition.

Example 14: Relative Pharmacokinetic Analysis

Comparative pharmacokinetic analysis of methocarbamol oral suspension of batch B3 was conducted with methocarbamol tablets in normal, healthy, adult human volunteers under fasting condition.

Relative pharmacokinetic analysis (i.e. geometric least squares means, ratio, 90% confidence interval, 95% upper confidence bound and power) of Test Product-T vs. Reference Product-R for methocarbamol are summarized in the following table:

TABLE 20

Relative pharmacokinetic results for methocarbamol

| Parameters (Units) | Geometric Least Squares Means | | Ratio (T/R) % | 90% Confidence Interval (%) | Intra Subject CV (%) | Power (T/R) (%) |
|---|---|---|---|---|---|---|
| | Test Product-T | Reference Product-R | | | | |
| Ln $C_{max}$ (ng/ml) | 15024.640 | 14942.355 | 100.55 | 82.02-123.27 | 32.09 | 56.60 |
| Ln $AUC_{0-t}$ (hr*ng/mL) | 32827.153 | 32913.450 | 99.74 | 92.85-107.14 | 11.03 | 99.87 |
| Ln $AUC_{0-\infty}$ (hr*ng/mL) | 33224.254 | 33275.895 | 99.84 | 93.03-107.16 | 10.89 | 99.88 |

As per results, the test product has demonstrated bioavailable to the reference product with respect to $C_{max}$, $AUC_{0-t}$ and $AUC_{0-\infty}$.

While aspects of the oral liquid formulation have been described in terms of its specific embodiments, certain modifications, and equivalents will be apparent to those skilled in the art, and are intended to be included within the scope of the claimed oral liquid formulation.

The subject matter of (1) International Application No. PCT/IB2024/059865, filed on Oct. 9, 2024, and (2) Indian patents application Nos. 202321067771 filed on Oct. 10, 2023, and 202421034276 filed on Apr. 30, 2024 is hereby incorporated by reference in its entirety to the extent necessary to understand the subject matter disclosed herein.

The invention claimed is:

1. An oral liquid formulation, comprising:
   an active pharmaceutical ingredient consisting of methocarbamol in an amount of about 150 mg/mL,
   a suspending agent comprising magnesium aluminum silicate in an amount of from about 1 mg/mL to about 25 mg/mL;
   one or more pH modifying agents;
   one or more pharmaceutically acceptable excipients selected from the group consisting of an antimicrobial agent, a viscosity modifying agent, a humectant, a sweetening agent, a flavoring agent, and a combination thereof; and
   water;
   wherein the oral liquid formulation is in the form of a suspension and has a pH of from about 2 to about 6.

2. The oral liquid formulation of claim 1, wherein the one or more pH modifying agents is selected from the group consisting of sodium citrate, sodium acetate trihydrate, phosphate, citric acid, tris, succinate, histidine, glycine, arginine, malic, tartaric, acetic, benzoic, gluconic, glyceric, lactic, adipic, ascorbic, carbonic, glutamic, ammonium chloride, triethanolamine, and salts or acids thereof, and a combination thereof.

3. The oral liquid formulation of claim 1, wherein the one or more pH modifying agents is present in an amount of from about 0.5 mg/mL to about 30 mg/mL.

4. The oral liquid formulation of claim 1, wherein the one or more pharmaceutically acceptable excipients comprise an antimicrobial agent selected from the group consisting of benzoic acid, potassium sorbate, sodium benzoate, chlorobutanol, butyl paraben, propyl paraben, methyl paraben, ethyl paraben, benzalkonium chloride, benzethonium chloride, benzyl alcohol, chlorobutanol, m-cresol, myristyl gamma picolinium chloride, phenol, 2-phenoxyethanol, phenyl mercuric nitrate, phenyl ethyl alcohol, EDTA, and a combination thereof.

5. The oral liquid formulation of claim 1, wherein the one or more pharmaceutically acceptable excipients comprise an antimicrobial agent in an amount of from about 0.01 mg/mL to about 20 mg/mL.

6. The oral liquid formulation of claim 1, wherein the one or more pharmaceutically acceptable excipients comprise an antimicrobial agent comprising sodium benzoate.

7. The oral liquid formulation of claim 1, wherein the one or more pharmaceutically acceptable excipients comprise a viscosity modifying agent selected from the group consisting of methyl cellulose, hydroxyethyl cellulose, bentonite, hectorite, microcrystalline cellulose, sodium carboxymethyl cellulose, hydroxy propyl methyl cellulose, xanthan gum, acacia, tragacanth, alginates, guar gum, colloidal silicon dioxide, and a combination thereof.

8. The oral liquid formulation of claim 1, wherein the one or more pharmaceutically acceptable excipients comprise a viscosity modifying agent in an amount of from about 1 mg/mL to about 25 mg/mL.

9. The oral liquid formulation of claim 1, wherein the one or more pharmaceutically acceptable excipients comprise a viscosity modifying agent comprising sodium carboxymethylcellulose.

10. The oral liquid formulation of claim 1, wherein the one or more pharmaceutically acceptable excipients comprise a humectant selected from the group consisting of glycerol, hyaluronic acid, salicylic acid, an alpha hydroxy acid, propylene glycol, honey, sorbitol, and a combination thereof.

11. The oral liquid formulation of claim 1, wherein the one or more pharmaceutically acceptable excipients comprise a humectant in an amount of from about 1 mg/mL to about 700 mg/mL.

12. The oral liquid formulation of claim 1, wherein the one or more pharmaceutically acceptable excipients comprise a humectant comprising glycerol.

13. The oral liquid formulation of claim 1, wherein the one or more pharmaceutically acceptable excipients comprise a sweetening agent selected from the group consisting of glucose, sucralose, trehalose, fructose, xylose, dextrose, galactose, tagatose, maltose, sucrose, glycerol, dulcitol, mannitol, lactitol, sorbitol, xylitol, saccharine or the corresponding sodium, potassium or calcium salt, cyclamate or the corresponding sodium or calcium salt, aspartame, or acesulfame or the potassium salt thereof, ammonium glycyrrhizinate, alitame, inulin, isomalt, neohesperidin dihydrochalcone, neotame, thaumatin, and a combination thereof.

14. The oral liquid formulation of claim 1, wherein the one or more pharmaceutically acceptable excipients comprise a sweetening agent in an amount of from about 1 mg/mL to about 50 mg/mL.

15. The oral liquid formulation of claim 1, wherein the one or more pharmaceutically acceptable excipients comprise a sweetening agent comprising sucralose.

16. The oral liquid formulation of claim 1, wherein the one or more pharmaceutically acceptable excipients comprise a flavoring agent in an amount of from about 0.01 mg/mL to about 5 mg/mL.

17. The oral liquid formulation of claim 1, wherein the oral liquid formulation has less than 1% methocarbamol related substance impurities after storage at 40° C.±2° C./75% RH or 25° C.±2° C./60% RH±5% RH or 30° C.±2° C./65% RH for 6 months.

18. The oral liquid formulation of claim 1, wherein the oral liquid formulation has a viscosity of from about 50 cps to about 700 cps.

19. The oral liquid formulation of claim 1, wherein the methocarbamol has a D(0.90) particle size of not more than about 150 μm.

20. A method for the treatment of, as adjunct to rest, physical therapy, and other measures for the relief and discomfort associated with acute, painful musculoskeletal conditions in a patient in need thereof, wherein said method comprises administering a therapeutically effective amount of an oral liquid formulation of claim 1 to a patient in need thereof.

* * * * *